United States Patent
Suzuki et al.

(10) Patent No.: US 10,398,392 B2
(45) Date of Patent: Sep. 3, 2019

(54) X-RAY CT APPARATUS, IMAGE PROCESSING DEVICE AND IMAGE RECONSTRUCTION METHOD

(71) Applicant: HITACHI, LTD., Tokyo (JP)

(72) Inventors: Tsuyoshi Suzuki, Tokyo (JP); Fuyuhiko Teramoto, Tokyo (JP); Yuko Aoki, Tokyo (JP); Taiga Goto, Tokyo (JP)

(73) Assignee: HITACHI, LTD., Tokyo (JP)

( * ) Notice: Subject to any disclaimer, the term of this patent is extended or adjusted under 35 U.S.C. 154(b) by 288 days.

(21) Appl. No.: 15/542,962

(22) PCT Filed: Feb. 1, 2016

(86) PCT No.: PCT/JP2016/052881
§ 371 (c)(1),
(2) Date: Jul. 12, 2017

(87) PCT Pub. No.: WO2016/129433
PCT Pub. Date: Aug. 18, 2016

(65) Prior Publication Data
US 2018/0110480 A1    Apr. 26, 2018

(30) Foreign Application Priority Data
Feb. 12, 2015 (JP) ................ 2015-024861

(51) Int. Cl.
*A61B 6/03* (2006.01)
*G06T 7/246* (2017.01)
(Continued)

(52) U.S. Cl.
CPC .......... *A61B 6/032* (2013.01); *A61B 6/5205* (2013.01); *G06T 1/0007* (2013.01); *G06T 5/002* (2013.01);
(Continued)

(58) Field of Classification Search
CPC ..... A61B 6/032; A61B 6/5205; G06T 11/006; G06T 7/246; G06T 7/97; G06T 1/0007;
(Continued)

(56) References Cited

U.S. PATENT DOCUMENTS 7,653,224 B2 * 1/2010 Goto ............. G06T 11/006
382/128
2006/0165211 A1   7/2006 Goto et al.
(Continued)

FOREIGN PATENT DOCUMENTS

JP   11-009582    1/1999
JP   2004-188163  7/2004
(Continued)

OTHER PUBLICATIONS

International Search Report dated May 10, 2016 in connection with PCT/JP2016/052881.

*Primary Examiner* — Christine S. Kim
(74) *Attorney, Agent, or Firm* — Cooper & Dunham LLP

(57) ABSTRACT

In order to provide an X-ray CT apparatus which can reconstruct a tomographic image with less unevenness in image quality at a high speed on the basis of projection data which is obtained by irradiating an object with X-rays, the X-ray CT apparatus of the invention includes an inverse projection phase width setting unit that sets an inverse projection phase width which is an angular width of projection data used for reconstruction, for each tomographic image, and a view weight calculation unit that calculates a view weight which is a weight coefficient multiplied by projection data within the inverse projection phase width and is a function of a view angle, for each position of a pixel of a tomographic image.

10 Claims, 13 Drawing Sheets

(51) Int. Cl.
  *G06T 7/00* (2017.01)
  *G06T 1/00* (2006.01)
  *G06T 5/00* (2006.01)
  *G06T 11/00* (2006.01)
  *A61B 6/00* (2006.01)
(52) U.S. Cl.
  CPC ............... *G06T 7/246* (2017.01); *G06T 7/97* (2017.01); *G06T 11/006* (2013.01); *G06T 11/008* (2013.01); *G06T 2207/10081* (2013.01)
(58) Field of Classification Search
  CPC ............... G06T 5/002; G06T 11/008; G06T 2207/10081
  See application file for complete search history.

(56) References Cited

U.S. PATENT DOCUMENTS

| | | |
|---|---|---|
| 2007/0189436 A1 | 8/2007 | Goto et al. |
| 2008/0273778 A1 | 11/2008 | Goto et al. |
| 2009/0110139 A1 | 4/2009 | Noshi et al. |
| 2010/0172564 A1* | 7/2010 | Hagiwara ............. G06T 11/006 382/131 |
| 2014/0029819 A1* | 1/2014 | Zeng .................... G06T 11/003 382/131 |
| 2014/0193055 A1* | 7/2014 | Takahashi ............. G06T 11/006 382/131 |
| 2015/0093003 A1 | 4/2015 | Goto et al. |

FOREIGN PATENT DOCUMENTS

| | | |
|---|---|---|
| JP | 2009-101086 | 5/2009 |
| JP | 2012-034972 | 2/2012 |
| JP | 2013-000479 | 1/2013 |
| WO | WO2005/077278 A1 | 8/2005 |
| WO | WO2005/122901 A1 | 12/2005 |
| WO | WO2013/161443 A1 | 10/2013 |

\* cited by examiner

X-RAY CT APPARATUS, IMAGE PROCESSING DEVICE AND IMAGE RECONSTRUCTION METHOD

TECHNICAL FIELD

The present invention relates to an X-ray computed tomography (CT) apparatus, and particularly to a technique of reconstructing a tomographic image with less unevenness in image quality at a high speed on the basis of obtained projection data.

BACKGROUND ART

An X-ray CT apparatus, which includes an X-ray source which irradiates an object with X-rays and an X-ray detector which detects a dose of X-rays transmitted through the object as projection data, reconstructs a tomographic image of the object by using pieces of projection data from a plurality of angles obtained by rotating the X-ray source and the X-ray detector around the object, and displays the reconstructed tomographic image. An image displayed by the X-ray CT apparatus draws a shape of an organ of an object, and is used for image diagnosis.

The image quality of a reconstructed tomographic image changes depending on the magnitude of an inverse projection phase width which is an angle width of projection data used for reconstruction. In other words, as the inverse projection phase width increases, noise decreases, and as the inverse projection phase width decreases, noise increases.

PTL 1 discloses a method for reducing noise of an obtained tomographic image and also reducing noise unevenness. In other words, in PTL 1, an appropriate inverse projection phase width is calculated for each position of a pixel of a tomographic image, a view weight which is a weight coefficient multiplied by projection data and is a function of a view angle is calculated according to the inverse projection phase width, and a tomographic image is reconstructed by using projection data multiplied by the view weight.

CITATION LIST

Patent Literature

PTL 1: International Publication No. 2013/161443

SUMMARY OF INVENTION

Technical Problem

However, in PTL 1, since the inverse projection phase width is calculated for each position of a pixel, and the view weight is calculated according to the calculated inverse projection phase width, noise of a tomographic image and noise unevenness are reduced, but a calculation load of the inverse projection phase width calculated for each position of a pixel increases, and, as a result, it takes time to reconstruct a tomographic image.

Therefore, an object of the invention is to provide an X-ray CT apparatus, an image processing device, and an image reconstruction method, capable of reconstructing a tomographic image with less unevenness in image quality at a high speed on the basis of obtained projection data.

Solution to Problem

In order to achieve the above-described object, according to the invention, an inverse projection phase width which is an angular width of projection data used for reconstruction is set for each tomographic image, and is fixed, a view weight which is multiplied by projection data within the inverse projection phase width is calculated for each position of a pixel of a tomographic image, and a tomographic image is reconstructed by using the calculated view weight.

Specifically, according to the invention, there is provided an X-ray CT apparatus including an X-ray source that irradiates an object with X-rays; an X-ray detector that detects a dose of X-rays having been transmitted through the object as projection data; a reconstruction unit that reconstructs a tomographic image of the object on the basis of the projection data; an inverse projection phase width setting unit that sets an inverse projection phase width which is an angular width of projection data used for reconstruction, for each tomographic image; and a view weight calculation unit that calculates a view weight which is a weight coefficient multiplied by projection data within the inverse projection phase width and is a function of a view angle, for each position of a pixel of a tomographic image.

Advantageous Effects of Invention

According to the invention, it is possible to provide an X-ray CT apparatus and an image reconstruction method, capable of reconstructing a tomographic image with less unevenness in image quality at a high speed on the basis of obtained projection data.

DESCRIPTION OF EMBODIMENTS

Figure 1:
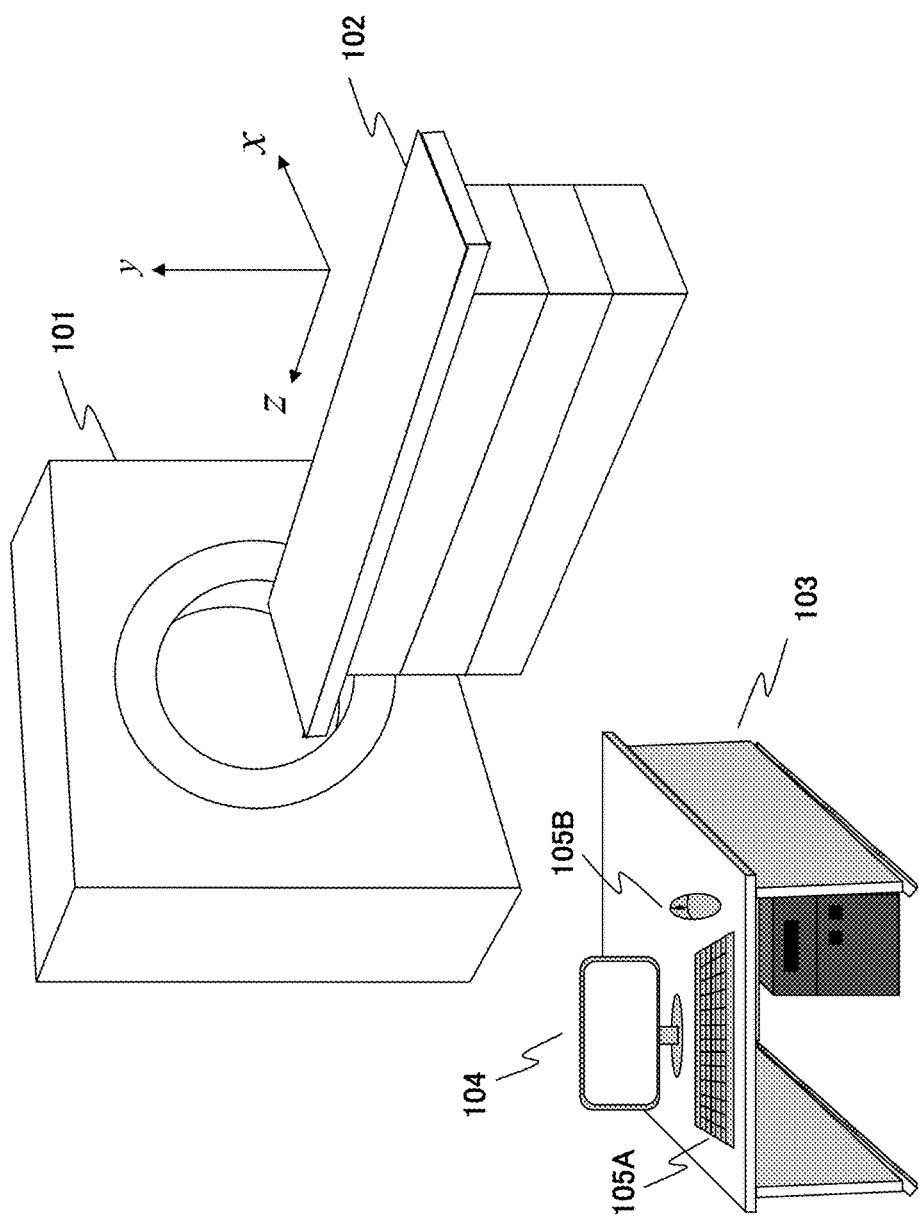
FIG. 1 is a diagram illustrating the entire configuration of an X-ray CT apparatus of the invention.

According to the invention, an X-ray CT apparatus includes an X-ray source that irradiates an object with X-rays; an X-ray detector that detects a dose of X-rays having been transmitted through the object as projection data; a reconstruction unit that reconstructs a tomographic image of the object on the basis of the projection data; an inverse projection phase width setting unit that sets an inverse projection phase width which is an angular width of projection data used for reconstruction, for each tomographic image; and a view weight calculation unit that calculates a view weight which is a weight coefficient multiplied by projection data within the inverse projection phase width and is a function of a view angle, for each position of a pixel of a tomographic image.

The view weight calculation unit includes a reference view weight generation unit that generates a view weight with a shape which is set according to the inverse projection phase width, as a reference view weight; and a view weight changing unit that changes a shape of the reference view weight by using a change formula which is defined on the basis of a distance between a position of a pixel of the tomographic image and a reference point.

The change formula includes a cubic function.

In a case where a value of the reference view weight is indicated by $w_1$, a value of a changed view weight is indicated by W, and an adjustment parameter is indicated by K, the change formula is expressed as follows:

$$W=0.5\cdot(K\cdot(2w_1-1)^3+(1-K)\cdot(2w_1-1))+1)$$

In a case where a distance between a position of a pixel of a tomographic image and a reference point is indicated by R, a boundary value of R in which K changes is indicated by L, and at $K_{max} \leq K_{min}$, the following expression is given:

$$K = \begin{cases} -\dfrac{K_{max} - K_{min}}{L} \cdot R + K_{max} & (0 \leq R \leq L) \\ K_{min} & (L < R) \end{cases}$$

The inverse projection phase width setting unit sets an inverse projection phase width according to a scanning part, and the coefficients $K_{max}$ and $K_{min}$ of the change formula are set for each scanning part, and are smoothly changed between respective scanning parts.

The change formula includes a triangular function.

The view weight calculation unit reconstructs two tomographic images for which time points of acquiring projection data are different from each other within a set inverse projection phase width, and sets prioritized image quality for each scanning part by using motion information which is acquired on the basis of the two tomographic images.

A value W of a view weight is expressed as follows by using φ' and adjustment parameters T and K:

$$W=T\cdot(K\cdot(2\phi'-1)^3+(1-K)\cdot(2\phi'-1)+(1))+(1-T),$$

φ' is obtained by using a view angle φ expressed by:

$$\phi' = \frac{\pi - |\phi|}{\pi}$$

In a case where a distance between a position of a pixel of a tomographic image and a reference point is indicated by R, a boundary value of R in which K changes is indicated by L, and at $K_{max} \leq K_{min}$, the following expression is given:

$$K = \begin{cases} -\dfrac{K_{max} - K_{min}}{L} \cdot R + K_{max} & (0 \leq R \leq L) \\ K_{min} & (L < R) \end{cases}$$

In a case where a distance from the rotation center to a slice position of a tomographic image is indicated by S, the maximum value of S in which projection data corresponding to one rotation can be used is indicated by $S_{360}$, and the maximum value of S in which at least one piece of projection data can be used is indicated by $S_{max}$, the following expression is given:

$$T = \begin{cases} 0 & (0 \leq S \leq S_{360}) \\ \dfrac{S - S_{360}}{S_{max} - S_{360}} & (S_{360} < S < S_{max}) \\ 1 & (S \geq S_{max}) \end{cases}$$

According to the invention, an image processing device which irradiates an object with X-rays, and reconstructs a tomographic image of the object by using projection data which is acquired on the basis of a dose of X-rays having been transmitted through the object, includes an inverse projection phase width setting unit that sets an inverse projection phase width which is an angular width of projection data used for reconstruction, for each tomographic image; and a view weight calculation unit that calculates a view weight which is a weight coefficient multiplied by projection data within the inverse projection phase width and is a function of a view angle, for each position of a pixel of a tomographic image.

According to the invention, an image reconstruction method includes an acquisition step of acquiring projection data of an object; a setting step of setting an inverse projection phase width which is an angular width of projection data used for reconstruction, for each tomographic image; a calculation step of calculating a view weight which is a weight coefficient multiplied by projection data within the inverse projection phase width and is a function of a view angle, for each position of a pixel of a tomographic image; and a reconstruction step of reconstructing a tomographic image of the object on the basis of data obtained by multiplying the projection data by the view weight.

Hereinafter, preferred embodiments of an X-ray CT apparatus according to the invention will be described in detail with reference to the accompanying drawings. In the following description and the accompanying drawings, constituent elements having the same functional configurations are given the same reference numerals, and repeated description will be omitted.

First Embodiment

Figure 2:
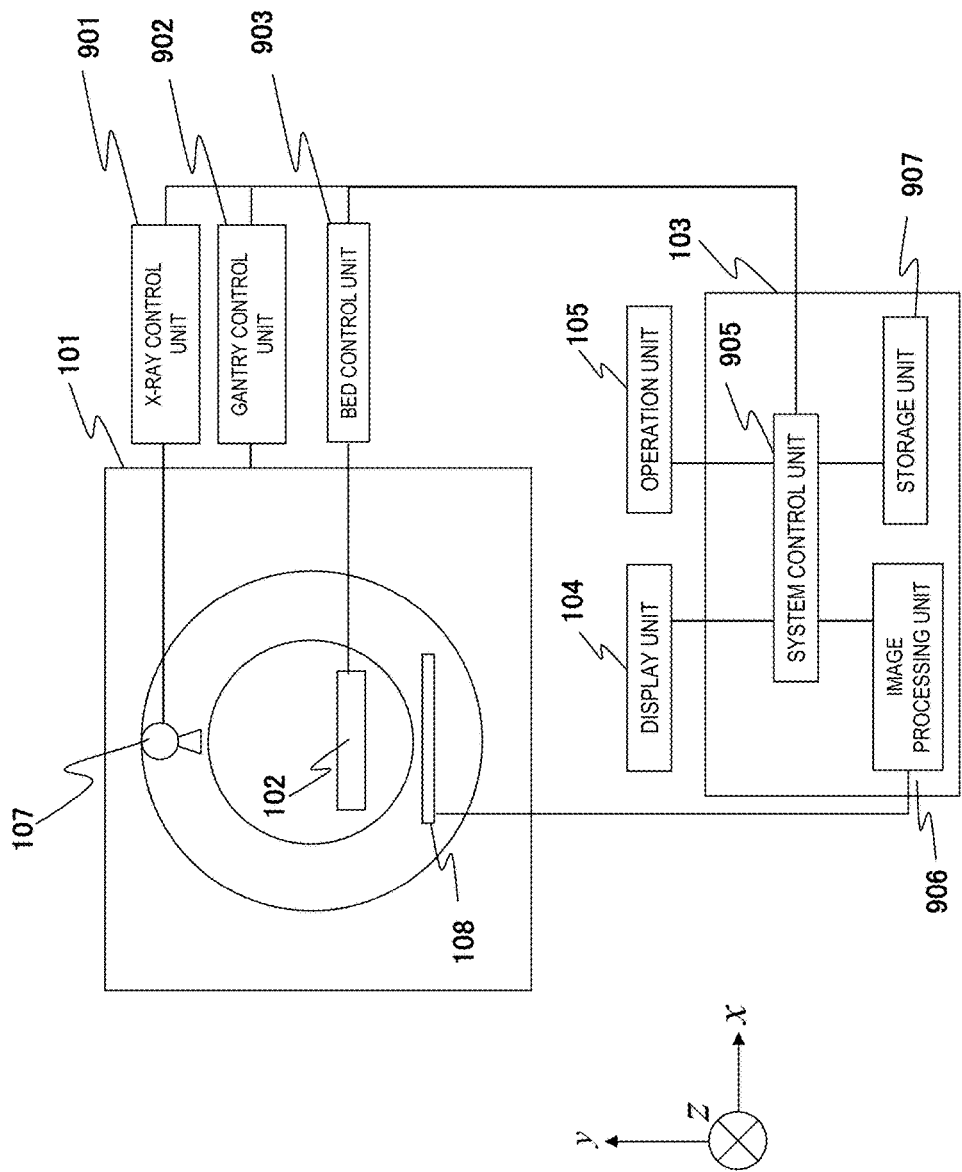
FIG. 2 is a diagram illustrating constituent elements of the X-ray CT apparatus of the invention.

FIG. 1 illustrates the entire configuration of an X-ray CT apparatus to which the invention is applied, and FIG. 2 illustrates constituent elements thereof. FIGS. 1 and 2 illustrate an XYZ coordinate system, and are used for supplementing the description.

The X-ray CT apparatus includes a scanner 101 and an operation console 103. The scanner 101 includes an X-ray tube bulb 107 which is an X-ray source generating X-rays; a bed 102; an X-ray detector 108 which detects X-rays having been transmitted through an object as projection data; an X-ray control unit 901; a gantry control unit 902; and a bed control unit 903. The X-ray tube bulb 107 is a device which irradiates an object with X-rays. The bed 102 is a device which carries the mounted object to a position where X-rays are applied. The X-ray detector 108 is a device which is disposed to oppose the X-ray tube bulb 107, and measures projection data which is a spatial distribution of transmitted X-rays by detecting X-rays having been transmitted through the object, and in which a plurality of X-ray detection elements are arranged in a two-dimensional manner.

The X-ray control unit 901 is a device which controls a current and a voltage which are input to the X-ray tube bulb 107. The gantry control unit 902 is a device which controls circumferential rotation operations of the X-ray tube bulb 107 and the X-ray detector 108 with a Z axis as a circumferential rotation axis. The bed control unit 903 is a device which controls movement of the bed 102 in respective directions such as an upward-and-downward direction, a front-and-rear direction, and a leftward-and-rightward direction, that is, a Y axis direction, a Z axis direction, and an X axis direction.

The operation console 103 includes a display unit 104, an operation unit 105 (a keyboard 105A and a mouse 105B), a system control unit 905, an image processing unit 906, and a storage unit 907. The display unit 104 displays a reconstruction condition setting screen or a reconstructed tomographic image. The keyboard 105A and the mouse 105B are used to input an object name, the examination date and time, and the like, or to operate a mouse pointer displayed on the display unit 104.

The image processing unit 906 is a calculation device which reconstructs a tomographic image by using projection data sent from the X-ray detector 108. The storage unit 907 is a device which preserves projection data obtained by the X-ray detector 108, image data of a tomographic image reconstructed by the image processing unit 906, scanning conditions, reconstruction conditions, and the like, and is, specifically, a hard disk drive (HDD). The system control unit 905 is a control unit which controls such devices and the X-ray control unit 901, the gantry control unit 902, and the bed control unit 903, and is configured to include, specifically, a calculation device. The system control unit 905 and the image processing unit 906 may execute a flow of a process which will be described later.

In the X-ray CT apparatus, generally, about 1000 scannings per circumference are performed in the circumferential rotation direction, and a single scanning is referred to as the-unit such as "one view". An aspect in which scanning is performed while the X-ray tube bulb 107 is rotated around an object in a state in which the bed 102 is fixed is called axial scanning, normal scanning, or conventional scanning since the X-ray tube bulb 107 draws a circular trajectory with respect to the object. An aspect in which scanning is performed while the X-ray tube bulb 107 is rotated around an object in a state in which the bed 102 is continuously moved in the circumferential rotation axis (Z axis) direction is called screw scanning, helical scanning, or spiral scanning since the X-ray tube bulb 107 draws a screw trajectory with respect to the object.

In the screw scanning, a distance which the bed 102 moves while the X-ray tube bulb 107 and the X-ray detector 108 are rotated once is defined as a "bed movement speed (mm/rotation)". In the screw scanning, when the entire length of the X-ray detector 108 in the circumferential rotation axis direction is assumed to be "1", a ratio of a distance which the bed 102 moves during one rotation is defined as a "table pitch". For example, in a case where the entire length of the X-ray detector 108 is 50 mm, and the bed 102 moves 25 mm during one rotation, "table pitch=0.5" is obtained, in a case where the bed 102 moves 50 mm, "table pitch=1.0" is obtained, and in a case where the bed 102 moves 75 mm, "table pitch=1.5" is obtained.

The table pitch is treated as an index indicating scanning performance, and, as a value of the table pitch becomes greater, the same range in the circumferential rotation axis direction can be scanned in a shorter period of time. As a value of the table pitch becomes greater, a scanning angular range at a position where the object is located becomes smaller, and thus an inverse projection phase width which is an angular width of projection data used for reconstruction also becomes smaller.

Figure 3:
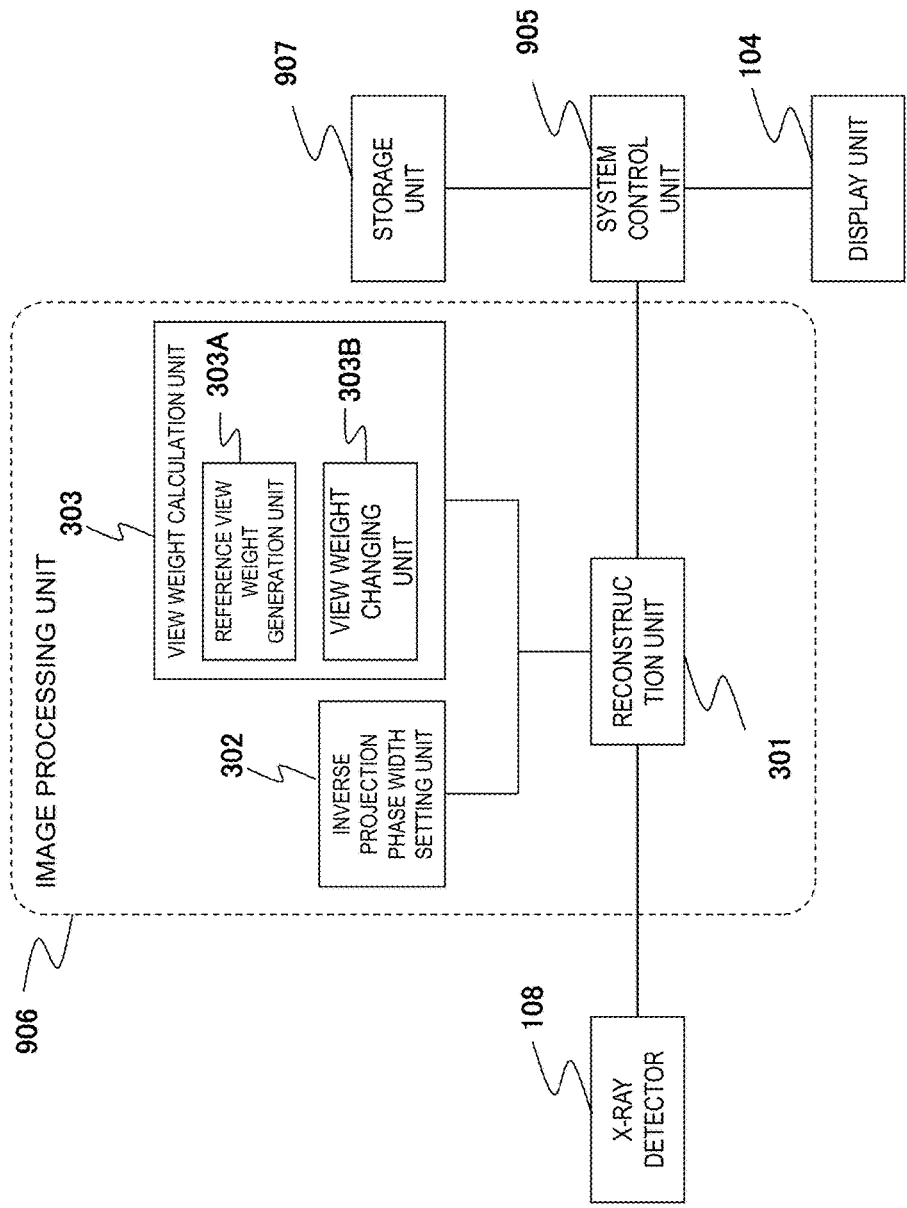
FIG. 3 is a functional configuration of a first embodiment.

Principal units of the present embodiment will be described with reference to FIG. 3. Such principal units may be formed by using dedicated hardware, and may be formed by using software operating on the image processing unit 906 or the system control unit 905. Here, a description will be made of a case of using software.

In the present embodiment, a reconstruction unit 301, an inverse projection phase width setting unit 302, and a view weight calculation unit 303 are provided. Hereinafter, each constituent unit will be described.

The reconstruction unit 301 reconstructs a tomographic image on the basis of projection data. An aspect of reconstruction is classified into four types such as reconstruction using 180-degree data (half scan data), reconstruction using 180 to 360-degree data (extended half scan data), reconstruction using 360-degree data (full scan data), and reconstruction using 360-degree or more data (over-scan data), according to inverse projection phase widths.

At least half scan data is required to reconstruct a tomographic image. In the reconstruction using half scan data, noise increases since an image is generated by using the minimum projection data, but a temporal resolution increases since a component of projection data in a time direction is reduced. An artifact due to slice extrapolation is reduced. On the other hand, as an inverse projection phase width which is an angular width of projection data used for reconstruction becomes larger, more projection data is used, and thus a tomographic image with less noise is obtained, but a temporal resolution deteriorates since a component of projection data in the time direction increases. An artifact due to slice extrapolation is increased.

The inverse projection phase width setting unit 302 sets an inverse projection phase width which is an angular width of projection data used for reconstruction, for each tomographic image. The inverse projection phase width is set on the basis of reconstruction conditions, and a value of an inverse number of a table pitch is set as the inverse projection phase width. A setting screen which will be described later may be used to set the inverse projection phase width.

The view weight calculation unit 303 calculates a view weight which is a weight coefficient multiplied by projection data within an inverse projection phase width and is a function of a view angle. As described above, at least half scan data is required to reconstruct a tomographic image, and, in a case of using half scan data, reconstruction is performed by uniformly using data corresponding to 180 degrees.

In contrast, in a case of using data corresponding to 180 degrees or more, projection data corresponding to a repeated view angle is presented, and thus reconstruction is performed by weighting each view. The view weight calculation unit 303 calculates a view weight for each position of a pixel on a tomographic image, and thus includes a reference view weight generation unit 303A and a view weight changing unit 303B.

The reference view weight generation unit 303A generates a view weight of a shape which is set according to a set inverse projection phase width, as a reference view weight. The inverse projection phase width is constant in a tomographic image, and thus reference view weights set for any tomographic images are the same as each other.

The view weight changing unit 303B changes the reference view weight generated by the reference view weight generation unit 303A to have an appropriate shape according to a position of a pixel of a tomographic image. The view weight changed to have the appropriate shape is multiplied by projection data within the inverse projection phase width, and data obtained as a result thereof is reconstructed by the reconstruction unit 301 so as to be generated as a tomographic image which is then displayed on the display unit 104 and to be used for diagnosis of an object.

Figure 4:
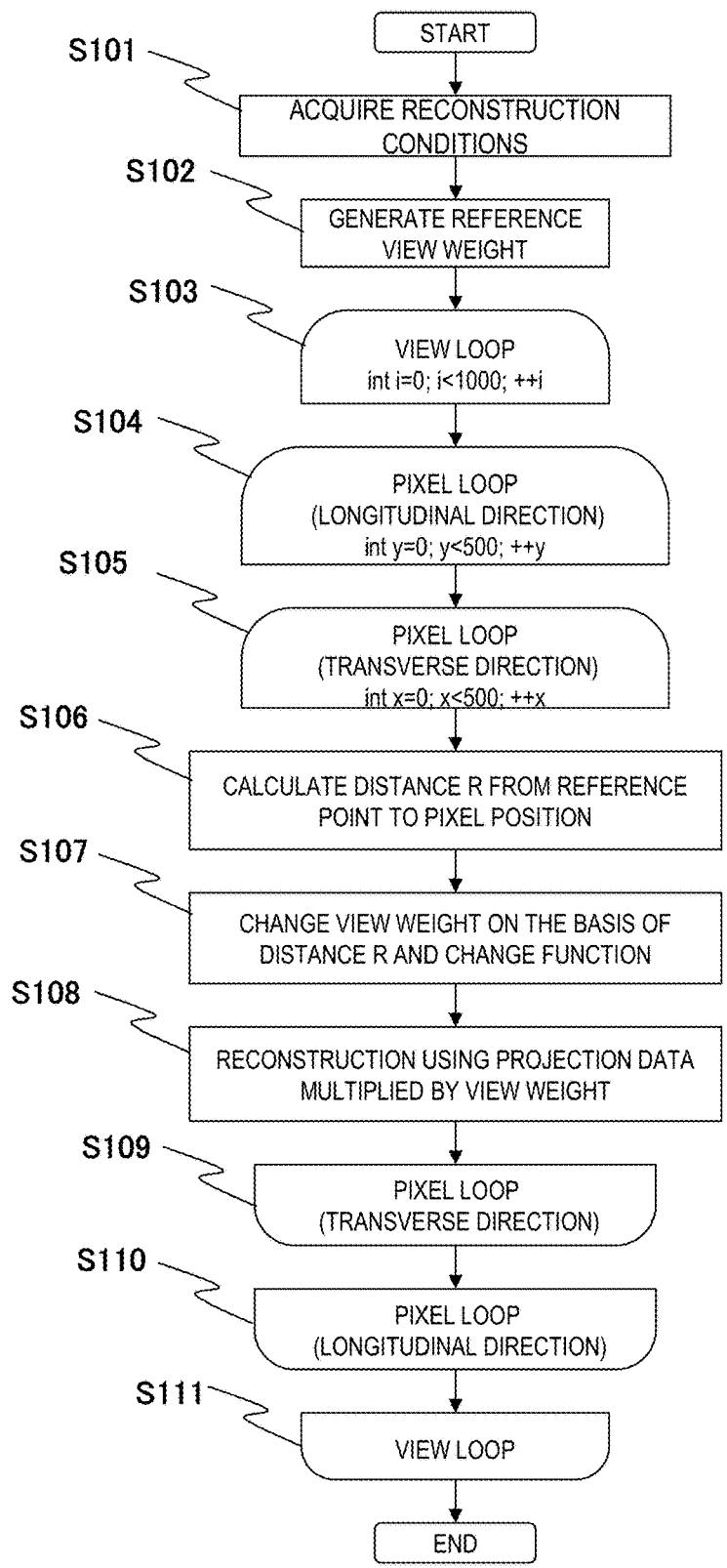
FIG. 4 is a diagram illustrating a flow of a process in the first embodiment.

With reference to FIG. 4, a description will be made of an example of a flow of a process performed by the X-ray CT apparatus including the above-described constituent elements.

Step S101

The system control unit 905 acquires reconstruction conditions. The reconstruction conditions may be acquired by receiving reconstruction conditions which are input from an operator via the operation unit 105, and may be acquired by reading reconstruction conditions stored in the storage unit 907.

Step S102

The reference view weight generation unit 303A generates a reference view weight. The inverse projection phase width setting unit 302 sets an inverse projection phase width before the reference view weight is generated. The inverse projection phase width setting unit 302 extracts, for example, a value of a table pitch from the reconstruction conditions acquired in step S101, and sets a value of an inverse number of the table pitch as the inverse projection phase width. Of course, a value which is different from an inverse number of the table pitch may be set as the inverse projection phase width. The reference view weight generation unit 303A generates a reference view weight according to the set inverse projection phase width.

Figure 5:
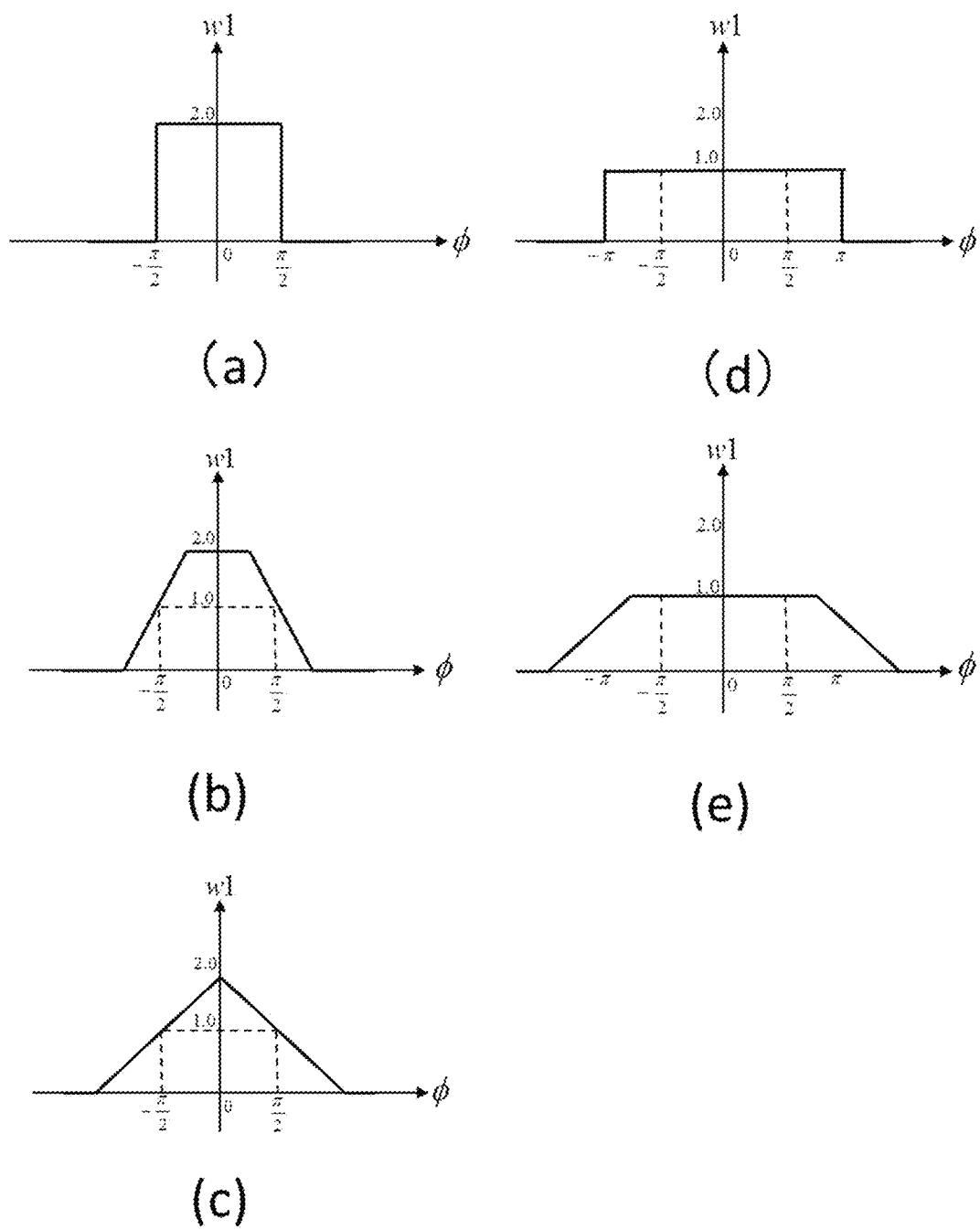
FIG. 5 is a diagram illustrating a reference view weight corresponding to an inverse projection phase width.

FIG. 5 illustrates examples of a reference view weight. In FIG. 5, a transverse axis expresses a view angle $\phi$, and a longitudinal axis expresses a weight coefficient $w_1$. In a case where the inverse projection phase width is 180 degrees, a reference view weight is rectangular as illustrated in FIG. 5(a). In a case where the inverse projection phase width is 180 to 360 degrees, a reference view weight is trapezoidal as illustrated in FIG. 5(b). In a case where the inverse projection phase width is 360 degrees, a reference view weight is triangular as illustrated in FIG. 5(c) or is rectangular as illustrated in FIG. 5(d). In a case where the inverse projection phase width is 360 degrees or more, a reference view weight is trapezoidal as illustrated in FIG. 5(e).

Step S103

In this step, a leading position of a view loop is shown, and 1000 views are assumed as an upper limit of a loop of the number of views corresponding to the inverse projection phase width.

Step S104

In this step, a leading position of a pixel loop of a tomographic image in a longitudinal direction (y direction) is shown, and 500 pixels are assumed as an upper limit of the pixel loop in the longitudinal direction.

Step S105

In this step, a leading position of a pixel loop of a tomographic image in a transverse direction (x direction) is shown, and 500 pixels are assumed as an upper limit of the pixel loop in the transverse direction.

Step S106

The view weight, changing unit 303B calculates distances from a reference point on a tomographic image to respective pixels. The following equation is used to calculate a distance R.

$$R = \sqrt{(x-x_r)^2 + (y-y_r)^2} \quad (1)$$

Here, it is assumed that a coordinate of the reference point is $(x_r, y_r)$, and a coordinate of a target pixel is $(x, y)$.

The reference point may be any point on a tomographic image, and may be, for example, the rotation center which is the circumferential rotation center of the X-ray tube bulb 107 and the X-ray detector 108, the center of an object, the reconstruction center, and a point designated by the operator.

Step S105

The view weight changing unit 303B changes the reference view weight on the basis of the distance R and a change function. In a case where a weight coefficient of a reference view weight for each view angle $\phi$ is indicated by $w_1$, and a weight coefficient after being changed is indicated by W, a change function $W(w_1)$ may satisfy the following three conditions. A range of $w_1$ is $0.0 < w_1 < 1.0$, and a range of W is $0.0 < W < 1.0$.

The coordinate $(w_1, W)$ passing through three points such as (0.0,0.0), (0.5,0.5), and (1.0,1.0) . . . (Condition 1)

The unevenness of a curve corresponding to $W(w_1)$ changing with (0.5,0.5) as a boundary . . . (Condition 2)

$W(w_1)$ being point symmetric with (0.5,0.5) as the center . . . (Condition 3)

An example of the change function $W(w_1)$ satisfying the conditions is shown in the following equation.

$$W = 0.5 \cdot (K \cdot (2w_1-1)^3 + (1-K) \cdot (2w_1-1) + 1) \quad (2)$$

Here, K indicates an adjustment parameter, and is a function of the distance R expressed by, for example, the following expression.

$$K = \begin{cases} -\dfrac{K_{max} - K_{min}}{L} \cdot R + K_{max} & (0 \leq R \leq L) \\ K_{min} & (L < R) \end{cases} \quad (3)$$

Here, $K_{max}$ is the maximum value of K, and is a value in a range of $-0.5 \leq K_{max} \leq 1.0$, $K_{min}$ is the minimum value of K, and is a value in a range of $-0.5 \leq K_{min} \leq K_{max}$, and L is a boundary value of the distance R in which K can change. L is set on the basis of, for example, a reconstruction field of view FOV, and is set as a half value of the maximum value of FOV. Expression (3) expresses a linear function, but a nonlinear function may be used.

Equation (2) is an equation including a cubic function of $w_1$, and a view weight can be changed without an excessive calculation load.

Figure 6:
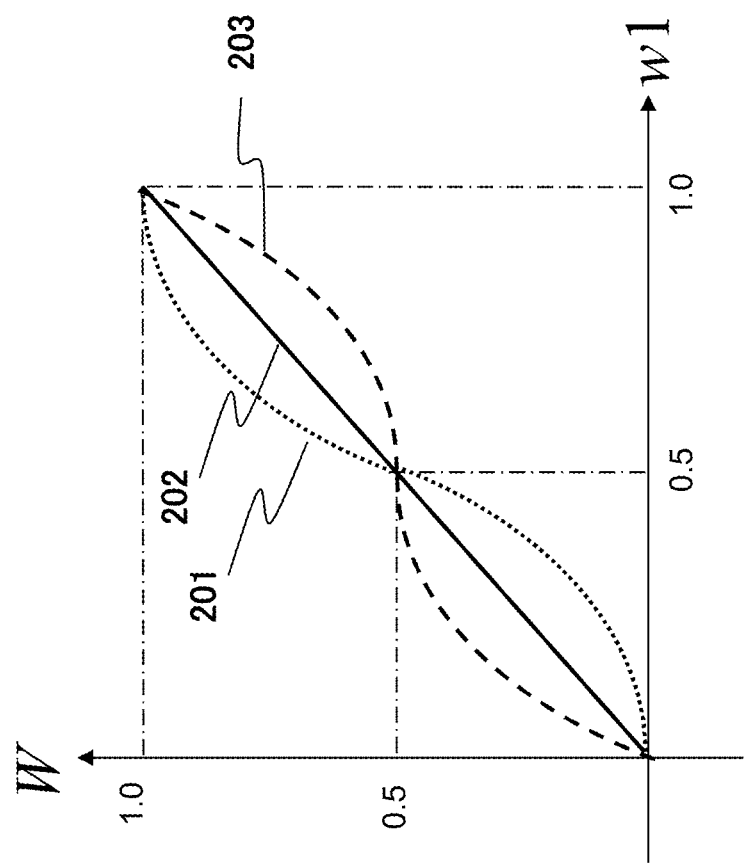
FIG. 6 is a diagram illustrating an example of a function for changing a shape of the reference view weight.

FIG. 6 illustrates an example of a graph obtained according to Equation (2). A dotted curve 201 is a graph corresponding to Equation (2) at K=−0.5, a solid straight line 202 is a graph at K=0.0, and a dashed curve 203 is a graph at K=1.0. It can be seen that all of the above (Condition 1), (Condition 2), and (Condition 3) are satisfied.

A change formula used in this step is not limited to Equation (2) as long as (Condition 1), (Condition 2), and (Condition 3) are satisfied, and, for example, the following expression or other expressions may be used.

$$W = \begin{cases} K' \cdot \sin(2\pi \cdot w_1) + w_1 & \left(0 \le R \le \frac{L'}{2}\right) \\ K' \cdot \sin(2\pi \cdot w_1 + \pi) + w_1 & \left(\frac{L'}{2} < R\right) \end{cases} \quad (4)$$

Here, K' is an adjustment parameter, and is a function of the distance R expressed by, for example, the following expression.

$$K' = \begin{cases} K'_{max} \cdot \dfrac{\left|R - \dfrac{L'}{2}\right|}{\dfrac{L'}{2}} & (0 \le R \le L') \\ K'_{max} & (L' < R) \end{cases} \quad (5)$$

Here, $K_{max}$ is the maximum value of K, and L' is a boundary value of the distance R in which K' can change.

Expression (4) is an expression including a triangular function of $w_1$, and a change formula can be expressed in a simple form.

Figure 7:
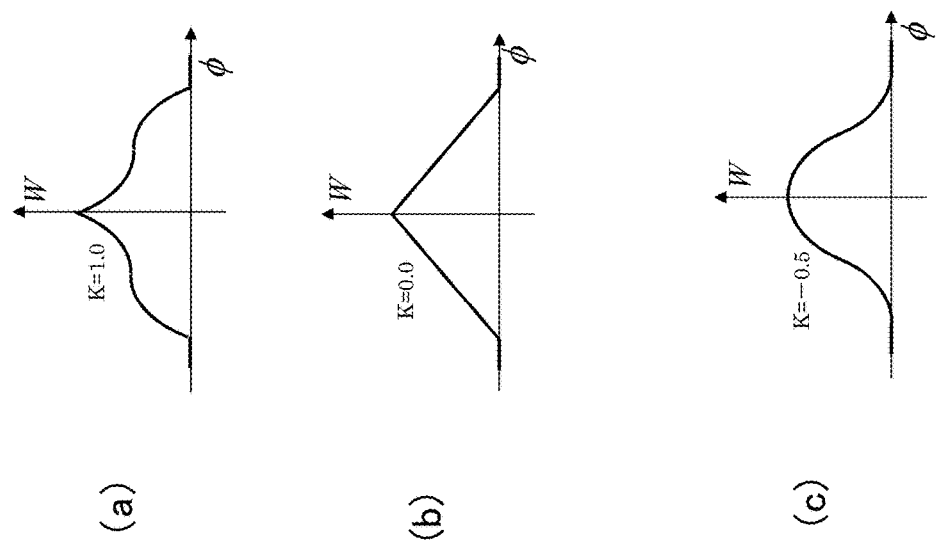
FIG. 7 is a diagram illustrating an example of a view weight adjusted according to a pixel position.

FIG. 7 illustrates examples in which the reference view weight illustrated in FIG. 5(c) is changed by using Equation (2). FIG. 7(a) illustrates a view weight at K=1.0, FIG. 7(b) illustrates a view weight, at K=0.0, and FIG. 7(c) illustrates a view weight at K=−0.5. FIG. 7 illustrates a state in which a view weight is changed as the distance R increases. In FIG. 7(a), a weight increases at both ends of the inverse projection phase width, whereas a weight decreases at both ends of the inverse projection phase width toward FIGS. 7(b) and 7(c). In other words, in a case where a reference point is the rotation center, there is the achievement of substantially the same effect as an effect in which the inverse projection phase width is set to be large for a pixel close to the rotation center, and the inverse projection phase width is set to be small for a pixel which is distant from the rotation center.

In the present embodiment, the same inverse projection phase width is set for all pixels on a tomographic image, but a view weight is appropriately adjusted for each pixel. Thus, noise can be reduced at the rotation center, and an artifact due to slice extrapolation can be reduced at a peripheral portion of the tomographic image. Since a view weight set for each pixel is gradually changed according to a distance from a reference point, image quality unevenness is also reduced.

Step S108

The reconstruction unit 301 reconstructs a tomographic image by using projection data multiplied by the changed view weight.

Step S109

This step indicates an end position of the pixel loop of the tomographic image in the transverse direction (x direction), and forms a pair with step S105.

Step S110

This step indicates an end position of the pixel loop of the tomographic image in the longitudinal direction (y direction), and forms a pair with step S104.

Step S111

This step indicates an end position of the view loop, and forms a pair with step S103.

In the present embodiment, an inverse projection phase width is not calculation in triple loops, and thus an excessive calculation load is not required.

The above-described flow of the process is executed by the X-ray CT apparatus, and thus it is possible to reconstruct a tomographic image with less image quality unevenness at a high speed.

Figure 8:
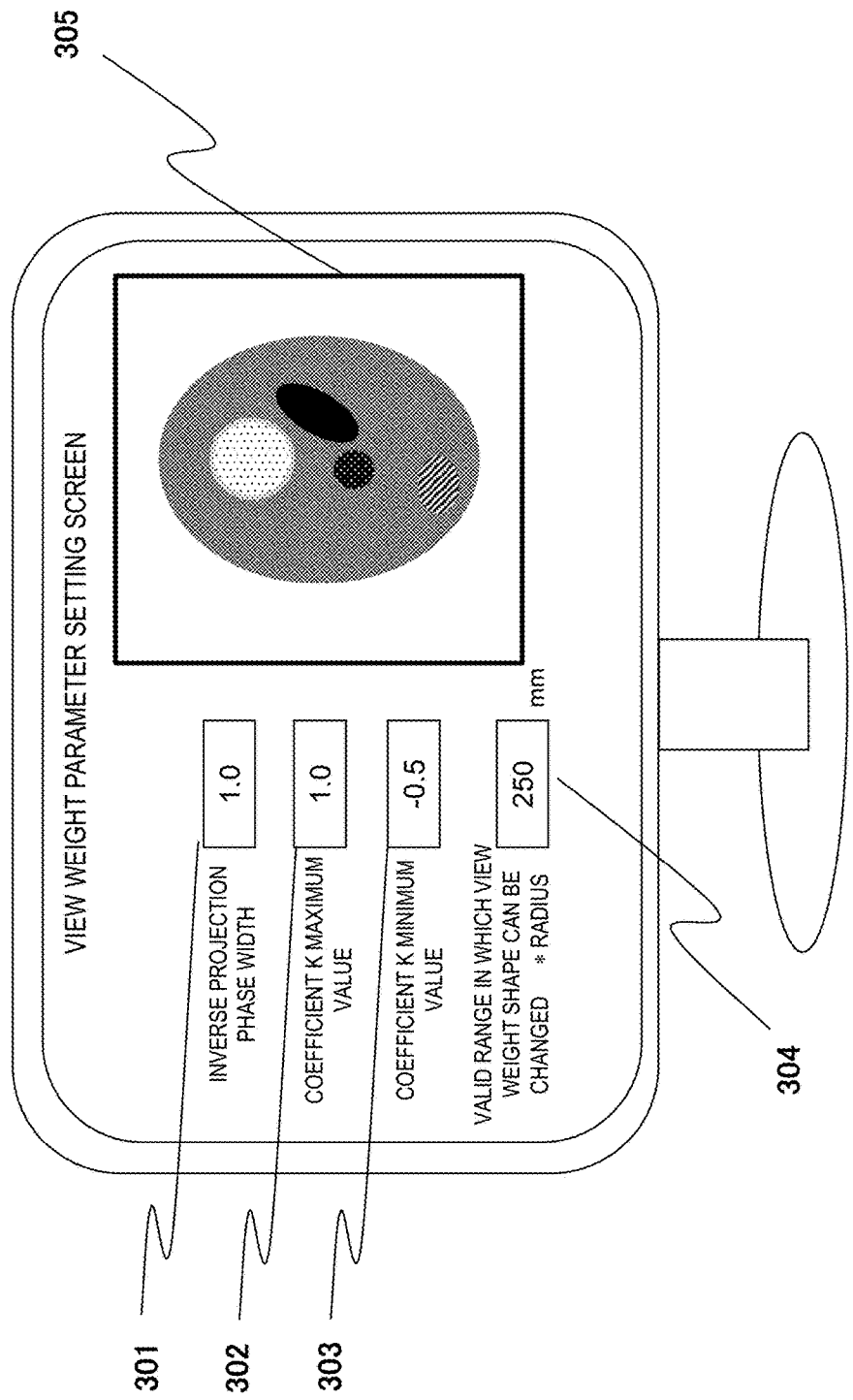
FIG. 8 is a diagram illustrating an example of a parameter setting screen in the first embodiment.

Preferably, various parameters used in a change formula can be freely set by an operator via the operation unit. FIG. 8 illustrates an example of a setting screen used for setting various parameters. The setting screen illustrated in FIG. 8 includes not only an input column 301 for an inverse projection phase width, an input column 302 for the maximum value of the coefficient K, an input column 303 for the minimum value of the coefficient K, and an input column 304 for a valid range, but also a display region 305 for a tomographic image which is reconstructed by using set parameters. Since various parameters are set by using such a setting screen, the operator can adjust various parameters while checking a tomographic image in the display region 305.

Second Embodiment

Next, a second embodiment will be described. In the first embodiment, in step S102, an inverse projection phase width is uniquely set on the basis of a table pitch. A value of the inverse projection phase width has the great influence on a temporal resolution and noise, and thus appropriate image quality may not be obtained depending on a scanning part. For example, in a case where the heart is included in, a scanning part, the temporal resolution is prioritized, and in a case where a scanning part is the abdomen, noise reduction is prioritized. Therefore, in the present embodiment, an operator sets prioritized image quality for each scanning part, and sets a parameter for changing an inverse projection phase width or a view weight according to the setting.

Figure 9:
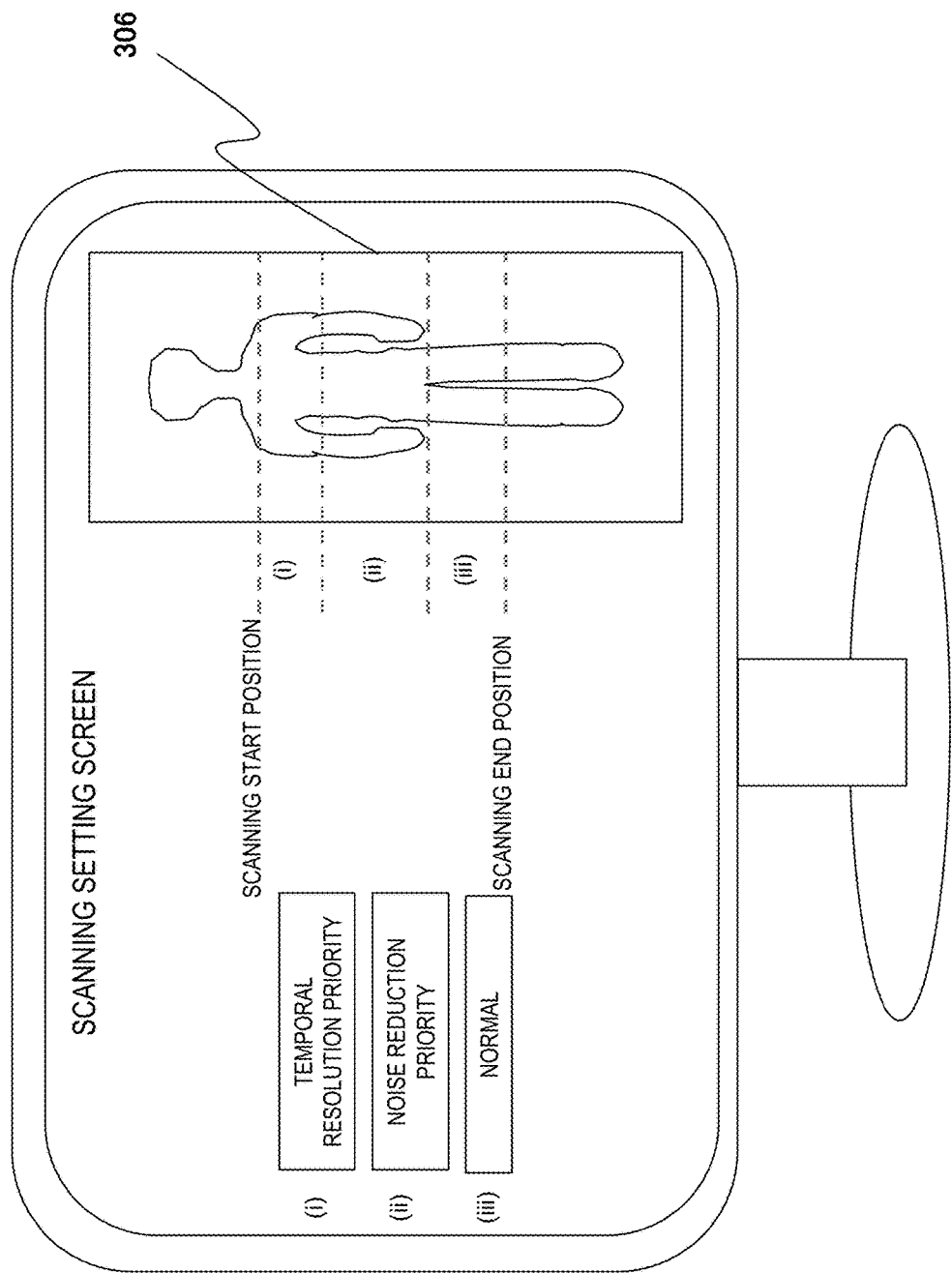
FIG. 9 is a diagram illustrating an example of a setting screen in a second embodiment.

FIG. 9 illustrates an example of a scanning setting screen used in the present embodiment. This screen displays (i) temporal resolution priority, (ii) noise reduction priority, and (iii) normal as options for prioritized image quality along with a display region 306 for a scanogram image. The option of (i) temporal resolution priority is used to set a scanning part which prioritizes a temporal resolution, the option of (ii) noise reduction priority is used to prioritize noise reduction, and the option of (iii) normal is used to make a balance between a temporal resolution and noise reduction. An image quality option is not limited thereto.

In the example illustrated in FIG. 9, (i) temporal resolution priority is set for the chest including the heart, (ii) noise reduction priority is set for the abdomen, and (iii) normal is set for the lower limbs. The image processing unit 906 operates the inverse projection phase width setting unit 302 or the view weight changing unit 303B according to these settings. Operations of the inverse projection phase width setting unit 302 and the view weight changing unit 303B are the same as those in the first embodiment except for the following description, and thus it is possible to reconstruct a tomographic image with less image quality unevenness at a high speed.

The inverse projection phase width setting unit 302 sets an inverse projection phase width according to setting on the scanning setting screen. In other words, the inverse projection phase width is set to be small for a scanning part for which (i) temporal resolution priority is set, the inverse projection phase width is set to be large for a scanning part for which (ii) noise reduction priority is set, and the inverse projection phase width is set to be between (i) and (ii) for a scanning part, for which (iii) normal is set.

Figure 10:
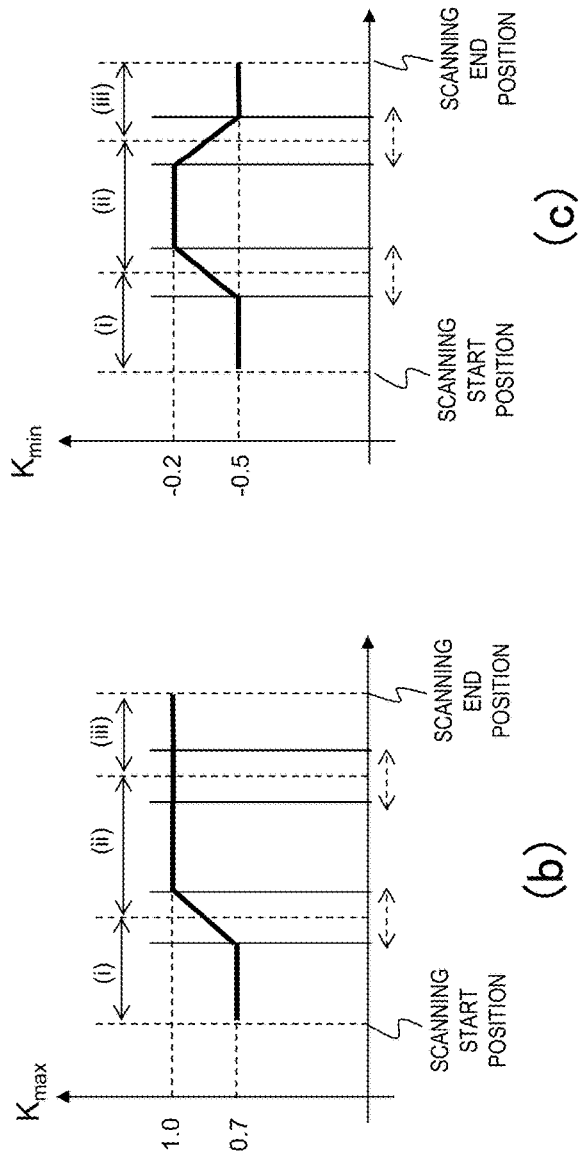
FIG. 10 is a diagram illustrating adjustment parameters in the second embodiment.

FIG. 10 illustrates an example of setting parameters in a case where the view weight changing unit 303 uses the change formula in Equation (2) based on Expression (3). As illustrated in FIG. 10(a), $K_{max}$=0.7 and $K_{min}$=−0.5 are set for (i) temporal resolution priority, $K_{max}$=1.0 and $K_{min}$=−0.2 are set (ii) noise reduction priority, and $K_{max}$=1.0 and $k_{min}$=−0.5 are set (iii) normal. With the above-described settings, in (i) temporal resolution priority, a weight of projection data which is temporally separated as in the view weight as illustrated in FIG. 7(c) can be reduced, and in (ii) noise reduction priority, weights of all pieces of projection data can be made uniform as in the view weight illustrated in FIG. 7(a).

As in FIGS. 10(b) and 10(c), each parameter may be smoothly changed between respective scanning parts indicated by dashed arrows. Each parameter is smoothly changed between respective scanning parts, and thus, it is possible to prevent image quality from being rapidly changed in a body axis direction of an object.

As described above, according to the present embodiment, an operator can set prioritized image quality for each scanning part, and it is also possible to reconstruct a tomographic image with image quality corresponding to the setting at a high speed.

Third Embodiment

Next, a third embodiment will be described. In the second embodiment, an operator sets prioritized image quality for each, scanning part. In the present embodiment, the view weight calculation unit 303 acquires motion information for each scanning part, and sets prioritized image quality for each scanning part on the basis of the acquired motion information.

Figure 11:
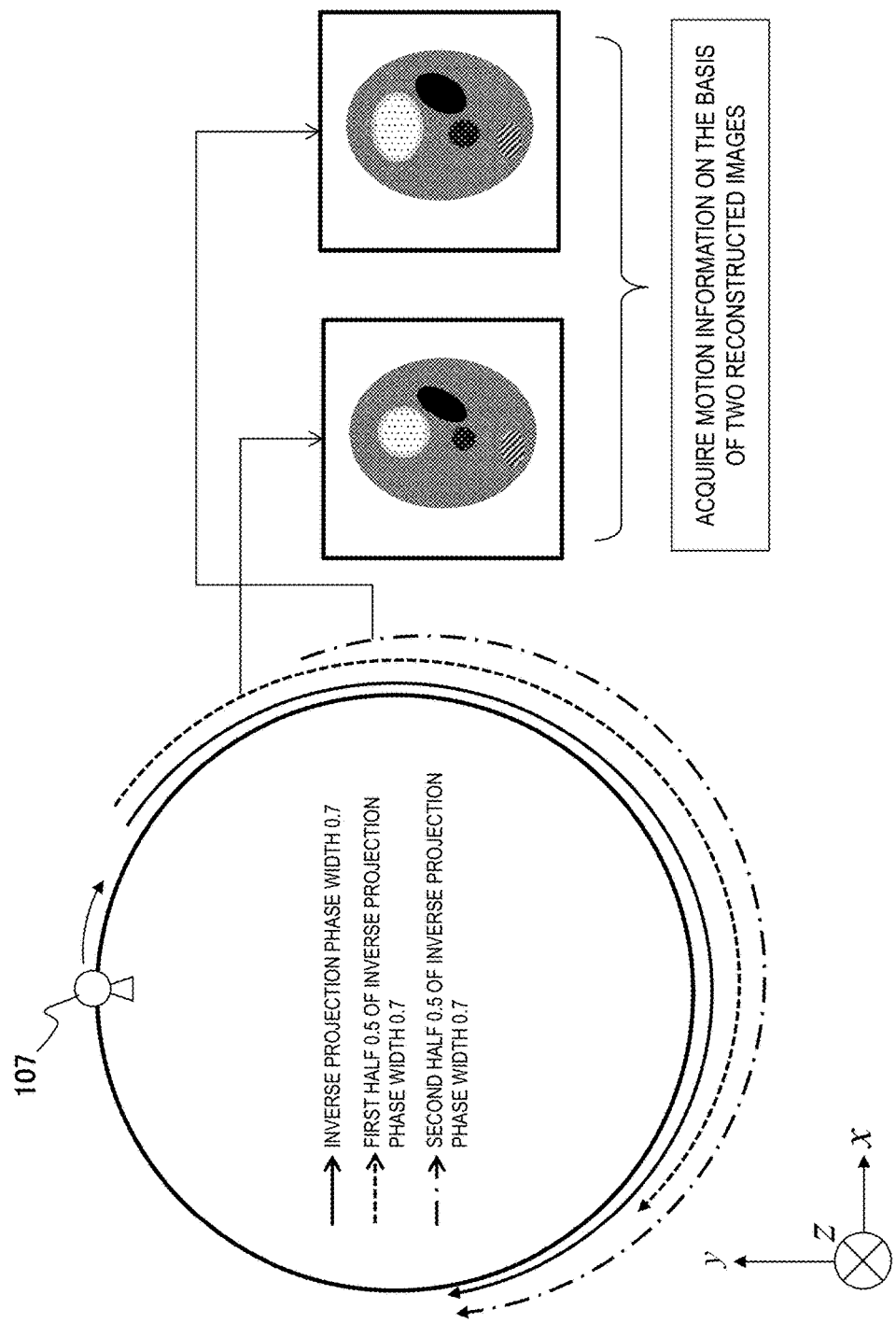
FIG. 11 is a diagram illustrating motion information acquisition in a third embodiment.

FIG. 11 is a diagram illustrating a method for acquiring motion information. A case of a tomographic image in which an inverse projection phase width can be set to a value greater than 0.5, for example, an inverse projection phase width of 0.7 can be set, is assumed. In FIG. 11, the range is indicated by a solid arrow. Since an inverse projection phase width is preferably 0.5 when a tomographic image is reconstructed, tomographic images can be respectively reconstructed in a range of a dotted arrow corresponding to a first half of 0.5 within the range indicated by the solid arrow and in a range of a dot-chain arrow corresponding to a second half of 0.5.

In other words, it is possible to reconstruct two tomographic images for which time points of acquiring projection data are different from each other.

If there is no motion in the range indicated by the solid arrow, that is, in the range in which the inverse projection phase width is 0.7, deviation does not occur between the two tomographic images, and if there is motion, deviation corresponding to the motion occurs. In other words, if a difference between both of the tomographic images is calculated, motion information in the inverse projection phase width of 0.7 can be acquired. In the present embodiment, it is set whether a temporal resolution is prioritized or noise is prioritized according to a difference value between two tomographic images. For example, if the difference is great, the temporal resolution is prioritized, and if the difference is small, noise is prioritized.

According to the present embodiment, since prioritized image quality is set for each tomographic image, prioritized image quality is set for each scanning part without troubling hands of an operator, and thus it is also possible to reconstruct a tomographic image with image quality corresponding to the setting at a high speed.

Fourth Embodiment

Next, a fourth embodiment will be described. In the first to third embodiments, a description has been made of reconstruction of projection data acquired through screw scanning. In the present embodiment, a description will be made of reconstruction of projection data acquired through axial scanning.

Figure 12:
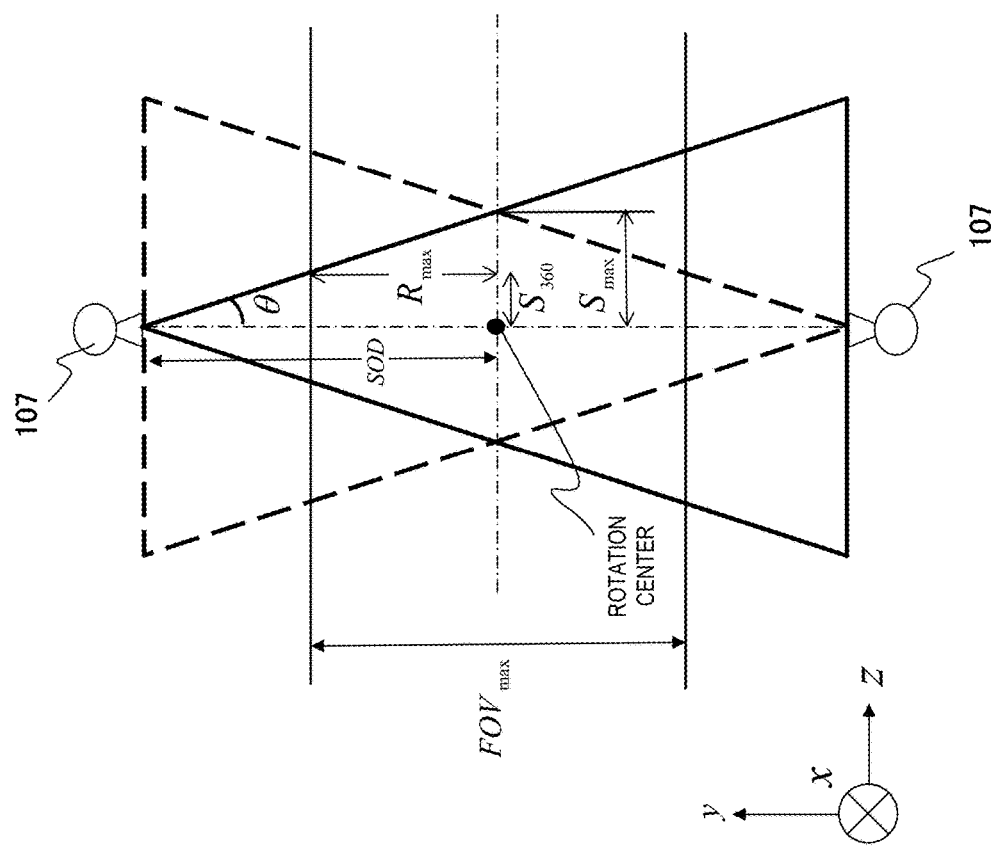
FIG. 12 is a diagram illustrating a relationship between a range of projection data acquired during axial scanning and a slice position.

With reference to FIG. 12, a description will be made of a relationship between a range of projection data acquired during axial scanning and a slice position. FIG. 12 illustrates an irradiation range (solid line) of X-rays at a view angle of 0 degrees and an irradiation range (dotted line) at 180 degrees in the X-ray tube bulb 107. Projection data corresponding to 360 degrees can be used in a region where two irradiation ranges overlap each other, but projection data is insufficient in other regions. In a case where a slice position in the Z axis direction with the rotation center as the origin is indicated by S, a distance from the X-ray tube bulb 107 to the rotation center is indicated by SOD, a half value of the maximum value $FOV_{max}$ of a reconstruction field of view (FOV) is indicated by $R_{max}$, and a half value of a cone angle is indicated by θ, the maximum value $S_{360}$ of S which can be reconstructed by using projection data corresponding to $FOV_{max}$ of 360 degrees is expressed by the following equation.

$$S_{100} = \frac{SOD \cdot \tan\theta - SOD + R_{max}}{SOD} \qquad (6)$$

The maximum value $S_{max}$ of S in which at least one piece of projection data can be used is expressed by the following equation.

$$S_{max} = SOD \cdot \tan\theta \qquad (7)$$

In other words, projection data corresponding to 360 degrees cannot be obtained in the range of the slice position S from $S_{360}$ to $S_{max}$, and thus an artifact increases due to slice extrapolation as S increases. Therefore, in the present embodiment, a view weight is calculated so that an artifact due to slice extrapolation is reduced. In the present embodiment, a tomographic image is reconstructed by using a view weight expressed by the following equation.

$$W = T \cdot (K \cdot (2\phi'-1)^3 + (1-K) \cdot (2\phi'-1) + 1) + (1-T) \qquad (8)$$

Here, φ indicates a view angle, K and T are adjustment parameters, and Expression (10) is the same as Expression (3).

$$\phi' = \frac{\pi - |\phi|}{\pi} \qquad (9)$$

$$K = \begin{cases} -\dfrac{K_{max} - K_{min}}{L} \cdot R + K_{max} & (0 \le R \le L) \\ K_{min} & (L < R) \end{cases} \qquad (10)$$

$$T = \begin{cases} 0 & (0 \le S \le S_{360}) \\ \dfrac{S - S_{360}}{S_{max} - S_{360}} & (S_{360} < S < S_{max}) \\ 1 & (S \ge S_{max}) \end{cases} \qquad (11)$$

Equation (8) is a formula for calculating a view weight on the basis of a distance from the rotation center, and includes a cubic function.

Figure 13:
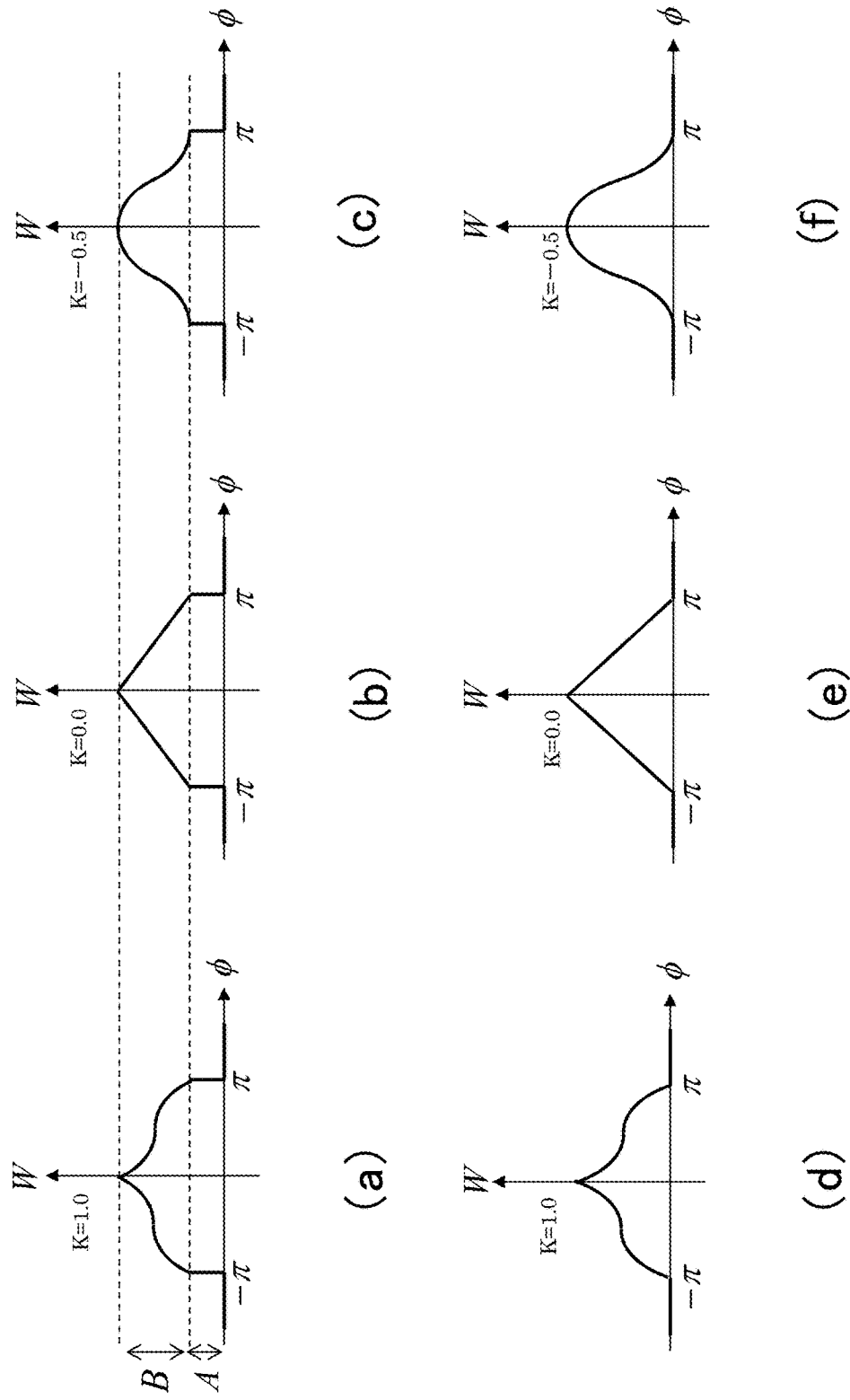
FIG. 13 is a diagram illustrating an example of an adjusted view weight in a fourth embodiment.

FIG. 13 illustrates examples of a view weight W calculated by using Equation (8). FIGS. 13(a) to 13(c) illustrate view weights at $S_{360} < S < S_{max}$, and FIGS. 13(d) to 13(f) illustrate view weights in a case where S is substantially $S_{max}$. Values of K are the same as illustrated in FIG. 13. In the range of $S_{360} < S < S_{max}$, a ratio between a range of A and a range of B in the FIGS. changes according to a value of S, a proportion of A increases as S comes close to $S_{360}$, and thus a shape of the view weight comes close to a rectangular shape. On the other hand, a proportion of B increases as S comes close to $S_{max}$, and thus FIGS. 13(d) to 13(f) are obtained.

As mentioned above, since a rectangular view weight is smoothly changed to a nonlinear view weight according to the slice position S of a reconstructed image, it is possible to prevent a rapid change in noise unevenness due to a difference in a slice position while reducing an artifact due to slice extrapolation. In other words, it is possible to make noise unevenness smooth in the Z axis direction when an MPR image is created.

The X-ray CT apparatus of the invention is not limited to the above-described embodiments, and constituent elements may be modified and embodied within the scope without departing from the spirit of the invention. A plurality of constituent elements described in the above-described embodiments may be combined with each other as appropriate.

REFERENCE SIGNS LIST

101 SCANNER, 102 BED, 103 OPERATION CONSOLE, 104 DISPLAY UNIT, 105 OPERATION UNIT, 105A KEYBOARD, 105B MOUSE, 107 X-RAY TUBE BULB, 108 X-RAY DETECTOR, 901 X-RAY CONTROL UNIT, 902 GANTRY CONTROL UNIT, 903 BED CONTROL UNIT, 905 SYSTEM CONTROL UNIT, 906 IMAGE PROCESSING UNIT, 907 STORAGE UNIT, 401 RECONSTRUCTION unit, 402 INVERSE PROJECTION PHASE WIDTH SETTING unit, 403 VIEW WEIGHT CALCULATION unit, 303A REFERENCE VIEW WEIGHT GENERATION UNIT, 303B VIEW WEIGHT CHANGING UNIT, 201 CURVE AT COEFFICIENT K=−0.5, 202 STRAIGHT LINE AT COEFFICIENT K=0.0, 203 CURVE AT COEFFICIENT K=1.0, 301 INPUT COLUMN FOR INVERSE PROJECTION PHASE WIDTH, 302 INPUT COLUMN FOR MAXIMUM VALUE OF COEFFICIENT K, 303 INPUT COLUMN FOR MINIMUM VALUE OF COEFFICIENT K, 304 INPUT COLUMN FOR VALID RANGE, 305 DISPLAY REGION FOR TOMOGRAPHIC IMAGE, 306 DISPLAY REGION FOR SCANOGRAM IMAGE

The invention claimed is:

1. An X-ray CT apparatus comprising:
an X-ray source that irradiates an object with X-rays;
an X-ray detector that detects a dose of X-rays having been transmitted through the object as projection data;
a reconstruction unit that reconstructs a tomographic image of the object on the basis of the projection data;
an inverse projection phase width setting unit that sets an inverse projection phase width which is an angular width of projection data used for reconstruction, for each tomographic image; and
a view weight calculation unit that calculates a view weight which is a weight coefficient, multiplied by projection data within the inverse projection phase width and is a function of a view angle, for each position of a pixel of a tomographic image.

2. The X-ray CT apparatus according to claim 1, wherein the view weight calculation unit includes
a reference view weight generation unit that generates a view weight with a shape which is set according to the inverse projection phase width, as a reference view weight; and
a view weight changing unit that changes a shape of the reference view weight by using a change formula which is defined on the basis of a distance between a position of a pixel of the tomographic image and a reference point.

3. The x-ray CT apparatus according to claim 2, wherein the change formula includes a cubic function.

4. The X-ray CT apparatus according to claim 3, wherein, in a case where a value of the reference view weight, is indicated by $w_1$, a value of a changed view weight is indicated by W, and an adjustment parameter is indicated by K, the change formula is expressed as follows:

$$W = 0.5 \cdot (K \cdot (2w_1-1)^3 + (1-K) \cdot (2w_1-1) + 1),$$

and wherein, in a case where a distance between a position of a pixel of a tomographic image and a reference point is indicated by R, a boundary value of R in which K can change is indicated by L, and at $K_{max} \le K_{min}$, the following expression is given:

$$K = \begin{cases} -\dfrac{K_{max} - K_{min}}{L} \cdot R + K_{max} & (0 \le R \le L) \\ K_{min} & (L < R) \end{cases}.$$

5. The X-ray CT apparatus according to claim 4,
wherein the inverse projection phase width setting unit sets an inverse projection phase width according to a scanning part, and
wherein the coefficients $K_{max}$ and $K_{min}$ of the change formula are set for each scanning part, and are smoothly changed between respective scanning parts.

6. The X-ray CT apparatus according to claim 2, wherein the change formula includes a triangular function.

7. The X-ray CT apparatus according to claim 1,
wherein the view weight calculation unit reconstructs two tomographic images for which time points of acquiring projection data are different from each other within a set inverse projection phase width, and sets prioritized image quality for each scanning part by using motion information which is acquired on the basis of the two tomographic images.

8. The X-ray CT apparatus according to claim 1,
wherein a value W of a view weight is expressed as follows by using $\phi'$ and adjustment parameters T and K:

$$W = T \cdot (K \cdot (2\phi'-1)^3 + (1-K) \cdot (2\phi'-1) + (1) + (1-T),$$

$\phi'$ being obtained by using a view angle $\phi$ expressed by $$\phi' = \frac{\pi - |\phi|}{\pi},$$

wherein, in a case where a distance between a position of a pixel of a tomographic image and a reference point is indicated by R, a boundary value of R in which K can change is indicated by L, and at $K_{min} \leq K_{max}$, the following expression is given:

$$K = \begin{cases} -\frac{K_{max} - K_{min}}{L} \cdot R + K_{max} & (0 \leq R \leq L) \\ K_{min} & (L < R) \end{cases},$$

and
wherein, in a case where a distance from the rotation center to a slice position of a tomographic image is indicated by S, the maximum value of S in which projection data corresponding to one rotation can be used is indicated by $S_{360}$, and the maximum value of S in which at least one piece of projection data can be used is indicated by $S_{max}$, the following expression is given:

$$T = \begin{cases} 0 & (0 \leq S \leq S_{360}) \\ \frac{S - S_{360}}{S_{max} - S_{360}} & (S_{360} < S < S_{max}) \\ 1 & (S \geq S_{max}) \end{cases}.$$

9. An image processing device which irradiates an object with X-rays, and reconstructs a tomographic image of the object by using projection data which is acquired on the basis of a dose of X-rays having been transmitted through the object, the device comprising:

an inverse projection phase width setting unit that sets an inverse projection phase width which is an angular width of projection data used for reconstruction, for each tomographic image; and a view weight calculation unit that calculates a view weight which is a weight coefficient multiplied, by projection data within the inverse projection phase width and is a function of a view angle, for each position of a pixel of a tomographic image.

10. An image reconstruction method comprising:

an acquisition step of acquiring projection data of an object;

a setting step of setting an inverse projection phase width which is an angular width of projection data used for reconstruction, for each tomographic image;

a calculation step of calculating a view weight which is a weight coefficient multiplied by projection data within the inverse projection phase width and is a function of a view angle, for each position of a pixel of a tomographic image; and a reconstruction step of reconstructing a tomographic image of the object on the basis of data obtained by multiplying the projection data by the view weight.

* * * * *